(12) United States Patent
Brannan

(10) Patent No.: US 12,408,981 B2
(45) Date of Patent: Sep. 9, 2025

(54) MICROWAVE GENERATOR WITH DYNAMIC CORRECTION OF TEMPERATURE MEASUREMENTS

(71) Applicant: Covidien LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 440 days.

(21) Appl. No.: 18/014,851

(22) PCT Filed: Aug. 13, 2021

(86) PCT No.: PCT/US2021/046018
§ 371 (c)(1),
(2) Date: Jan. 6, 2023

(87) PCT Pub. No.: WO2022/036268
PCT Pub. Date: Feb. 17, 2022

(65) Prior Publication Data
US 2023/0285076 A1    Sep. 14, 2023

Related U.S. Application Data

(60) Provisional application No. 63/065,555, filed on Aug. 14, 2020.

(51) Int. Cl.
*A61B 18/18*  (2006.01)
*A61B 18/00*  (2006.01)

(52) U.S. Cl.
CPC ............... *A61B 18/1815* (2013.01); *A61B 2018/00577* (2013.01); *A61B 2018/00642* (2013.01);
(Continued)

(58) Field of Classification Search
CPC ...... A61B 18/1815; A61B 2017/00115; A61B 2018/00577; A61B 2018/00642;
(Continued)

(56) References Cited

U.S. PATENT DOCUMENTS 9,121,774 B2 *   9/2015   Brannan ............... G01J 5/0837
9,517,103 B2 *  12/2016   Panescu ................. A61B 5/068
(Continued)

FOREIGN PATENT DOCUMENTS

EP      3155995 A2     4/2017
WO   2018200865 A1    11/2018

OTHER PUBLICATIONS

International Search Report and Written Opinion dated Jan. 5, 2022, issued in corresponding international applicaton No. PCT/US2021/046018, 12 pages.

*Primary Examiner* — Michael F Peffley
(74) *Attorney, Agent, or Firm* — Carter, DeLuca & Farrell LLP

(57) ABSTRACT

A method for calculating a corrected temperature value (RTP corrected). The method includes determining a measured temperature value from a remote thermocouple probe (RTP measured), determining a temperature value of a remote thermocouple module (RTM), determining a temperature value of a system controller module (SCM), determining a temperature value of a microwave module (MWM), and calculating the corrected temperature value (RTP corrected). The corrected temperature value (RTP corrected) is based on the determined temperature value of the remote thermocouple probe (RTP measured), the determined temperature value of the system controller module (SCM), and at least one of the determined temperature value of the remote thermocouple module (RTM) or the determined temperature value of the microwave module (MWM).

20 Claims, 9 Drawing Sheets

(52) U.S. Cl.
CPC ............... *A61B 2018/00702* (2013.01); *A61B 2018/00714* (2013.01); *A61B 2018/00821* (2013.01); *A61B 2018/1823* (2013.01)

(58) Field of Classification Search
CPC .. A61B 2018/0066; A61B 2018/00702; A61B 2018/00714; A61B 2018/00779; A61B 2018/00785; A61B 2018/00815; A61B 2018/00821; A61B 2018/00892; A61B 2018/00988; A61B 2018/1823; A61B 2018/1869; A61B 90/90
See application file for complete search history.

(56) References Cited

U.S. PATENT DOCUMENTS

| | | | |
|---|---|---|---|
| 11,090,114 B2* | 8/2021 | Williams | ........... A61B 18/1815 |
| 2015/0105765 A1* | 4/2015 | Panescu | ................ A61B 18/12 |
| | | | 606/34 |
| 2018/0008346 A1 | 1/2018 | Williams | |

* cited by examiner

US 12,408,981 B2

MICROWAVE GENERATOR WITH DYNAMIC CORRECTION OF TEMPERATURE MEASUREMENTS

CROSS-REFERENCE TO RELATED APPLICATION

This application claims the benefit of the filing date of provisional U.S. Patent Application No. 63/065,555, filed Aug. 14, 2020.

INTRODUCTION

The present disclosure relates to microwave generators and, more specifically, to a microwave generator that dynamically corrects temperature measurement errors, for example, by compensating for inaccurate measurements caused by parasitic junctions and/or other factors.

BACKGROUND

In microwave ablation, an electromagnetic field is used to heat and destroy tumor cells. Treatment may involve inserting an ablation probe into tissues where cancerous tumors have been identified. Once the ablation probe is properly positioned, the ablation probe induces an electromagnetic field within the tissue surrounding the ablation probe to ablate the tissue.

Typically, systems for microwave ablation procedures include a microwave generator and a microwave instrument such as an ablation probe having an antenna assembly. The microwave generator and microwave instrument are operatively coupled to each other by a coaxial cable for carrying microwave signals from the microwave generator to the microwave instrument. Microwave generators typically include circuitry for generating microwave signals and a controller for controlling the operation of the circuitry and controlling a user interface, such as a display. The user interface includes user controls for setting characteristics of the microwave signals, such as controls for adjusting the power level and activation time of the microwave signals.

Microwave ablation systems may use thermocouples (TC) to measure temperature of tissue or devices. For example, needle-like remote thermocouple probes may be used to measure the tissue temperature adjacent to or within an ablation zone to monitor therapy delivery progress. The systems may also use a TC to measure the internal temperature of the ablation probe antenna assembly to confirm the probe is adequately cooled throughout the ablation procedure. Several factors may cause such temperature measurements to be inaccurate.

SUMMARY

In accordance with aspects of the disclosure, a method for calculating a corrected temperature value (RTP corrected) by a microwave generator is provided. The method includes determining a measured temperature value from a remote thermocouple probe (RTP measured), determining a temperature value of a remote thermocouple module (RTM), determining a temperature value of a system controller module (SCM), determining a temperature value of a microwave module (MWM), and calculating the corrected temperature value (RTP corrected). The corrected temperature value (RTP corrected) is calculated based on the determined temperature value of the remote thermocouple probe (RTP measured), the determined temperature value of the system controller module (SCM), and at least one of the determined temperature value of the remote thermocouple module (RTM) or the determined temperature value of the microwave module (MWM).

In an aspect, the corrected temperature value (RTP corrected) is calculated using the formula:

$$\text{RTP corrected} = \text{RTP measured} - C1*(\text{RTM} - \text{SCM}),$$
where $C1 = 0.3$.

In an aspect, the method includes determining whether the microwave generator is in an idle state or an active state.

In an aspect, when it is determined that the microwave generator is in the idle state, the corrected temperature value (RTP corrected) is calculated using the formula:

$$\text{RTP corrected} = \text{RTP measured} - C1*(\text{RTM} - \text{SCM}),$$
where $C1 = 0.3$.

Additionally, or alternatively, when it is determined that the microwave generator is in the active state, the corrected temperature value (RTP corrected) is calculated using the formula:

$$\text{RTP corrected} = \text{RTP measured} - C2*(\text{MWM} - \text{SCM}),$$
where $C1 = 0.13$.

In an aspect, when it is determined that the microwave generator is in the idle state and not within 120 seconds of deactivation, the corrected temperature value (RTP corrected) is calculated using the formula:

$$\text{RTP corrected} = \text{RTP measured} - C1*(\text{RTM} - \text{SCM}),$$
where $C1 = 0.3$.

Additionally, or alternatively, when it is determined that the microwave generator is in the idle state and within 120 seconds of deactivation, the corrected temperature value (RTP corrected) is calculated using the formula:

$$\text{RTP corrected} = \text{RTP measured} - C6*(\text{RTM} - \text{SCM}),$$
where $C6 = 0.19$.

In an aspect, when it is determined that the microwave generator is in the active state and within 10 seconds of activation, the corrected temperature value (RTP corrected) is calculated using the formula:

$$\text{RTP corrected} = \text{RTP measured} - C1*(\text{RTM} - \text{SCM}) - C2*(\text{MWM} - \text{SCM}), \text{ where } C1 = 0.3 \text{ and } C2 = 0.26.$$

In an aspect, when it is determined that the microwave generator is in the active state and between 10 to 30 seconds of activation, the corrected temperature value (RTP corrected) is calculated using the formula:

$$\text{RTP corrected} = \text{RTP measured} - C1*(\text{RTM} - \text{SCM}) - C3*(\text{MWM} - \text{SCM}), \text{ where } C1 = 0.3 \text{ and } C3 = 0.21.$$

In an aspect, when it is determined that the microwave generator is in the active state and between 30 to 120 seconds of activation, the corrected temperature value (RTP corrected) is calculated using the formula:
RTP corrected = RTP measured $- C1*(\text{RTM} - \text{SCM}) - C4*(\text{MWM} - \text{SCM})$, where $C1 = 0.3$ and $C4 = 0.15$.

In an aspect, when it is determined that the microwave generator is in the active state and after 120 seconds of activation, the corrected temperature value (RTP corrected) is calculated using the formula:

$$\text{RTP corrected} = \text{RTP measured} - C1*(\text{RTM} - \text{SCM}) - C5*(\text{MWM} - \text{SCM}), \text{ where } C1 = 0.3 \text{ and } C5 = 0.09.$$

In an aspect, the method includes determining an elapsed activation time (T) and an output power level of the microwave generator (P), wherein the corrected temperature value (RTP corrected) is calculated using the formula:

$$\text{RTP corrected} = \text{RTP measured} - C1*(\text{RTM} - \text{SCM}) - P*1/T*C2*(\text{MWM} - \text{SCM}), \text{ where } C1 = 0.3 \text{ and } C2 = 0.02.$$

In accordance with another aspect of the disclosure, a microwave generator is provided. The microwave generator includes a system controller module configured to control the microwave generator, a microwave module configured to generate microwave energy, and a remote thermocouple module configured to determine a temperature value of a remote thermocouple probe (RTP measured). At least one of the system controller module or the remote thermocouple module is configured to determine a temperature value of the remote thermocouple module (RTM), determine a temperature value of the system controller module (SCM), determine a temperature value of the microwave module (MWM), and calculate a corrected temperature value (RTP corrected). At least one of the system controller module or the remote thermocouple module is configured to calculate a corrected temperature value (RTP corrected) based on the determined temperature value of the remote thermocouple probe (RTP measured), the determined temperature value of the system controller module (SCM), and at least one of the determined temperature value of the remote thermocouple module (RTM) or the determined temperature value of the microwave module (MWM).

In an aspect, the corrected temperature value (RTP corrected) is calculated using the formula:

$$\text{RTP corrected} = \text{RTP measured} - C1*(\text{RTM} - \text{SCM}), \text{ where } C1 = 0.3.$$

In an aspect, at least one of the system controller module or the remote thermocouple module is configured to determine whether the microwave generator is in an idle state or an active state.

In an aspect, when it is determined that the microwave generator is in the idle state, the corrected temperature value (RTP corrected) is calculated using the formula:

$$\text{RTP corrected} = \text{RTP measured} - C1*(\text{RTM} - \text{SCM}), \text{ where } C1 = 0.3.$$

Additionally, or alternatively, when it is determined that the microwave generator is in the active state, the corrected temperature value (RTP corrected) is calculated using the formula:

$$\text{RTP corrected} = \text{RTP measured} - C2*(\text{MWM} - \text{SCM}), \text{ where } C1 = 0.13.$$

In an aspect, when it is determined that the microwave generator is in the idle state and not within 120 seconds of deactivation, the corrected temperature value (RTP corrected) is calculated using the formula:

$$\text{RTP corrected} = \text{RTP measured} - C1*(\text{RTM} - \text{SCM}), \text{ where } C1 = 0.3.$$

Additionally, or alternatively, when it is determined that the microwave generator is in the idle state and within 120 seconds of deactivation, the corrected temperature value (RTP corrected) is calculated using the formula:

$$\text{RTP corrected} = \text{RTP measured} - C6*(\text{RTM} - \text{SCM}), \text{ where } C6 = 0.19.$$

In an aspect, when it is determined that the microwave generator is in the active state and within 10 seconds of activation, the corrected temperature value (RTP corrected) is calculated using the formula:

$$\text{RTP corrected} = \text{RTP measured} - C1*(\text{RTM} - \text{SCM}) - C2*(\text{MWM} - \text{SCM}), \text{ where } C1 = 0.3 \text{ and } C2 = 0.26.$$

In an aspect, when it is determined that the microwave generator is in the active state and between 10 to 30 seconds of activation, the corrected temperature value (RTP corrected) is calculated using the formula:

$$\text{RTP corrected} = \text{RTP measured} - C1*(\text{RTM} - \text{SCM}) - C3*(\text{MWM} - \text{SCM}), \text{ where } C1 = 0.3 \text{ and } C3 = 0.21.$$

In an aspect, when it is determined that the microwave generator is in the active state and between 30 to 120 seconds of activation, the corrected temperature value (RTP corrected) is calculated using the formula:

$$\text{RTP corrected} = \text{RTP measured} - C1*(\text{RTM} - \text{SCM}) - C4*(\text{MWM} - \text{SCM}), \text{ where } C1 = 0.3 \text{ and } C4 = 0.15.$$

Additionally, or alternatively, when it is determined that the microwave generator is in the active state and after 120 seconds of activation, the corrected temperature value (RTP corrected) is calculated using the formula:

$$\text{RTP corrected} = \text{RTP measured} - C1*(\text{RTM} - \text{SCM}) - C5*(\text{MWM} - \text{SCM}), \text{ where } C1 = 0.3 \text{ and } C5 = 0.09.$$

In an aspect, at least one of the system controller module or the remote thermocouple module is further configured to determine an elapsed activation time (T) and an output power level of the microwave generator (P). The corrected temperature value (RTP corrected) may be calculated using the formula:

$$\text{RTP corrected} = \text{RTP measured} - C1*(\text{RTM} - \text{SCM}) - P*1/T*C2*(\text{MWM} - \text{SCM}), \text{ where } C1 = 0.3 \text{ and } C2 = 0.02.$$

In accordance with another aspect of the present disclosure, a non-transitory computer-readable storage medium storing instructions, which when executed by a processor, cause the processor to perform a method for calculating a corrected temperature value is provided. The method includes determining a measured temperature value from a remote thermocouple probe (RTP measured), determining a temperature value of a remote thermocouple module (RTM), determining a temperature value of a system controller module (SCM), determining a temperature value of a microwave module (MWM), and calculating the corrected temperature value (RTP corrected). The corrected temperature value (RTP corrected) is calculated based on the determined temperature value of the remote thermocouple probe (RTP measured), the determined temperature value of the system controller module (SCM), and at least one of the determined temperature value of the remote thermocouple module (RTM) or the determined temperature value of the microwave module (MWM).

In an aspect, the corrected temperature value (RTP corrected) is calculated using the formula:

$$\text{RTP corrected} = \text{RTP measured} - C1*(\text{RTM} - \text{SCM}), \text{ where } C1 = 0.3.$$

In an aspect, the method includes determining whether the microwave generator is in an idle state or an active state.

In an aspect, when it is determined that the microwave generator is in the idle state, the corrected temperature value (RTP corrected) is calculated using the formula:

RTP corrected=RTP measured−$C1$*(RTM−SCM),
where $C1$=0.3.

Additionally, or alternatively, when it is determined that the microwave generator is in the active state, the corrected temperature value (RTP corrected) is calculated using the formula:

RTP corrected=RTP measured−$C2$*(MWM−SCM),
where $C1$=0.13.

In an aspect, when it is determined that the microwave generator is in the idle state and not within 120 seconds of deactivation, the corrected temperature value (RTP corrected) is calculated using the formula:

RTP corrected=RTP measured−$C1$*(RTM−SCM),
where $C1$=0.3.

Additionally, or alternatively, when it is determined that the microwave generator is in the idle state and within 120 seconds of deactivation, the corrected temperature value (RTP corrected) is calculated using the formula:

RTP corrected=RTP measured−$C6$*(RTM−SCM),
where $C6$=0.19.

In an aspect, when it is determined that the microwave generator is in the active state and within 10 seconds of activation, the corrected temperature value (RTP corrected) is calculated using the formula:

RTP corrected=RTP measured−$C1$*(RTM−SCM)−$C2$*(MWM−SCM), where $C1$=0.3 and $C2$=0.26.

In an aspect, when it is determined that the microwave generator is in the active state and between 10 to 30 seconds of activation, the corrected temperature value (RTP corrected) is calculated using the formula:

RTP corrected=RTP measured−$C1$*(RTM−SCM)−$C3$*(MWM−SCM), where $C1$=0.3 and $C3$=0.21.

In an aspect, when it is determined that the microwave generator is in the active state and between 30 to 120 seconds of activation, the corrected temperature value (RTP corrected) is calculated using the formula:

RTP corrected=RTP measured−$C1$*(RTM−SCM)−$C4$*(MWM−SCM), where $C1$=0.3 and $C4$=0.15.

In an aspect, when it is determined that the microwave generator is in the active state and after 120 seconds of activation, the corrected temperature value (RTP corrected) is calculated using the formula:

RTP corrected=RTP measured−$C1$*(RTM−SCM)−$C5$*(MWM−SCM), where $C1$=0.3 and $C5$=0.09.

In an aspect, the method includes determining an elapsed activation time (T) and an output power level of the microwave generator (P), wherein the corrected temperature value (RTP corrected) is calculated using the formula:

RTP corrected=RTP measured−$C1$*(RTM−SCM)−$P$*1/$T$*$C2$*(MWM−SCM), where $C1$=0.3 and $C2$=0.02.

BRIEF DESCRIPTION OF THE DRAWINGS

Various embodiments of the present disclosure are described herein with reference to the drawings wherein.

DETAILED DESCRIPTION

Particular embodiments of the present disclosure are described below with reference to the accompanying drawings. In the following description, well-known functions or constructions are not described in detail to avoid obscuring the present disclosure in unnecessary detail.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Microwave generators may perform several functions in addition to and relating to the main function of generating a microwave signal to be used by a microwave instrument. While additional features add utility to a microwave generator, they also require more power, use more processing resources, and add to the overall cost of manufacturing. The present disclosure relates to a modular microwave generator system that includes physical modules and components with decentralized and isolated processing to perform auxiliary functions associated with the microwave generator. One such component is an improved remote thermocouple module that dynamically calculates and outputs corrected temperature measurements by compensating for inaccurate temperature measurements, for example, caused by parasitic junctions in the generator and other factors.

The disclosure relates to compensation of parasitic thermocouple junctions in a microwave ablation generator thermocouple measurement circuit using digitally implemented algorithms in programmable logic (software and firmware). As described below, temperature measurements of printed circuit boards within the microwave generator, as well as the microwave generator operating state, are used as inputs to drive the correction algorithms. The correction methods utilize two or more temperature measurements in addition to the integrated circuit compensation and remote thermocouple probe measurement to reduce the measurement error to within an acceptable specification (e.g., +/−0.5 dC).

Figure 1:
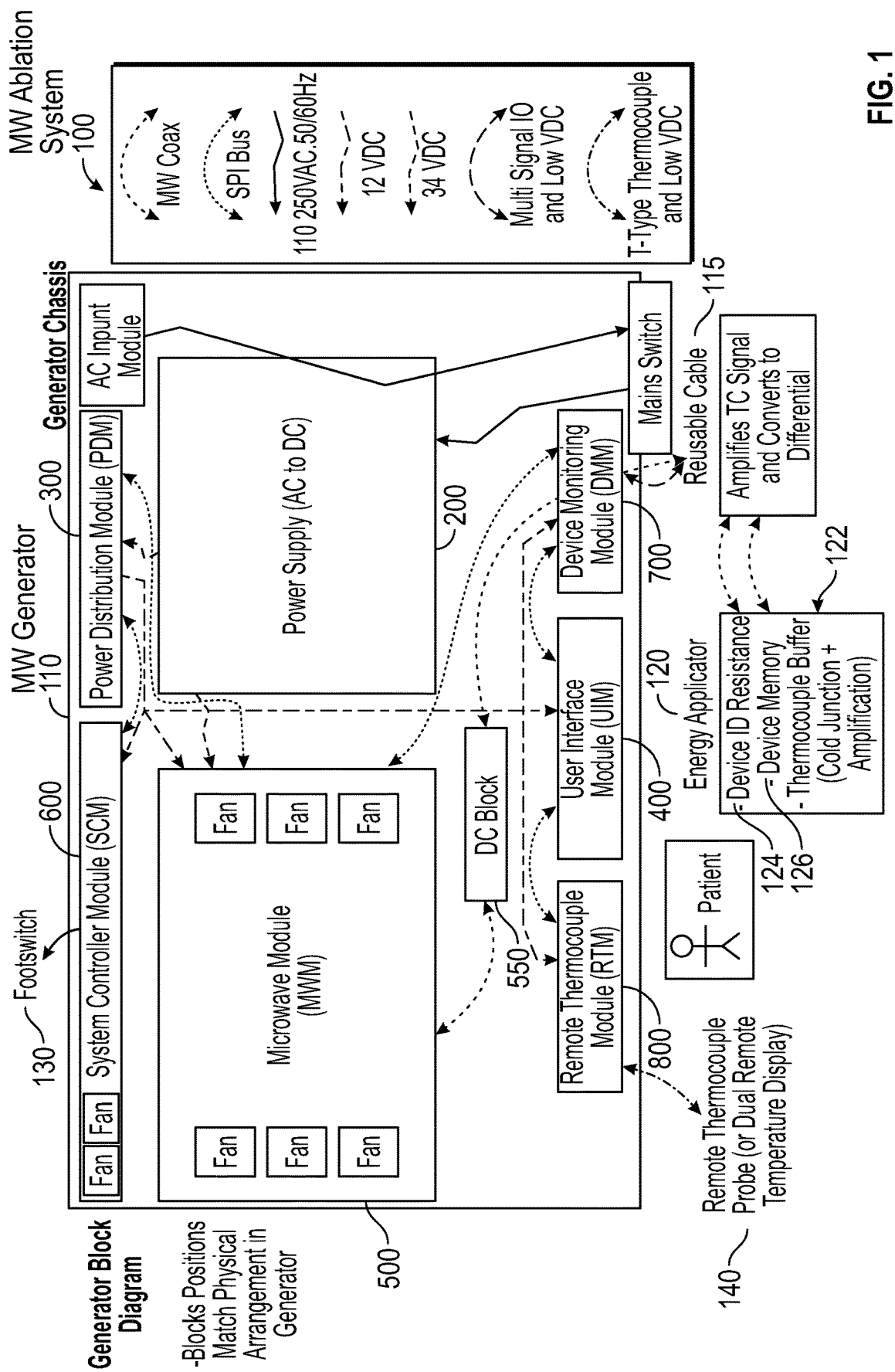
FIG. 1 is a block diagram of a microwave ablation system including a microwave generator.

FIG. 1 is a block diagram of a microwave ablation system in accordance with embodiments of the present disclosure. As shown in FIG. 1, the microwave ablation system 100 generally includes a microwave generator 110, an energy applicator 120 (e.g., a microwave ablation instrument such as a microwave antenna) connected to the microwave generator 110 by a reusable cable 115, a footswitch 130 for activating the output of the microwave generator 110, and a remote thermocouple probe 140 which may be directly coupled to the microwave generator 110 or may be coupled to the microwave generator 110 via a multi-probe temperature display unit (not shown). The energy applicator 120 includes a device ID module 122 having a device unique identification resistor ("DUIR") 124 and a device ID memory 126. The DUIR 124 has a device unique identification ("DUID") resistance that may be measured by the microwave generator 110 and compared to a resistance value indicator stored in memory of the microwave generator 110 to identify a type of the energy applicator 120. Based on the identified type of the energy applicator 120, a determination can be made as to whether or not the connected device is of the type that is compatible with the microwave generator 110. The device ID module 122 may be incorporated within the energy applicator 120 or may be incorporated within a separate connector or adapter configured to mate with a connector of the reusable cable 115. Thus, the reusable cable 115 may connect to the DUIR 124 and to the device ID memory 126 via connection to the energy applicator 120, or the reusable cable 115 may connect to the DUIR 124 and to the device ID memory 126, which, in turn, connect to the energy applicator 120. Similar memories and/or resistors storing device-specific information may be included in the reusable cable 115.

During the use of the microwave ablation system 100, a variety of different subsystems may be employed. Typically, the operation of the subsystems is controlled by a microprocessor-driven console (e.g., the microwave generator 110). The microprocessor receives mechanical inputs from the operator of the microwave ablation system 100 or from an assistant. A control input device, such as the footswitch 130, is used to accept mechanical inputs from the operator so that the operator can govern the operation of the subsystems within the microwave ablation system 100. When actuated by an operator, the control input device transmits electrical signals to the microprocessor control system. The electrical signals are then used to control the operational characteristics of a subsystem in the microwave ablation system 100.

As shown in FIG. 1, the microwave generator 110 is connected to a remote thermocouple probe 140. The remote thermocouple probe 140 may include a temperature sensor such as a thermocouple or a thermistor, and may include a memory storing a device ID or other information such as status information. The remote thermocouple probe 140 is operable to measure temperature of tissue at a surgical site. In one embodiment, the remote thermocouple probe 140 is configured to continuously output the temperature signal to the microwave generator 110 allowing the observation of the temperature and/or the control of the microwave generator 110 based on the temperature signal.

Microwave generator 110 may include any of, a subset of, or all of a power supply module 200, a power distribution module 300, a user interface module 400, a microwave module 500, a patient isolator 550, a system controller module 600, a device monitoring module 700, and a remote thermocouple module 800. Each of the modules or a subset of the modules of the microwave generator 110 communicate via a bus.

The power supply module 200 converts AC to DC and outputs DC voltage (e.g., 34 volts DC) to the power distribution module 300 and the microwave module 500. The power distribution module distributes a DC voltage (e.g., 12 volts DC) to power other modules of the microwave generator 110 including the user interface module 400, the system controller module 600, the device monitoring module 700, and the remote thermocouple module 800.

Figure 2:
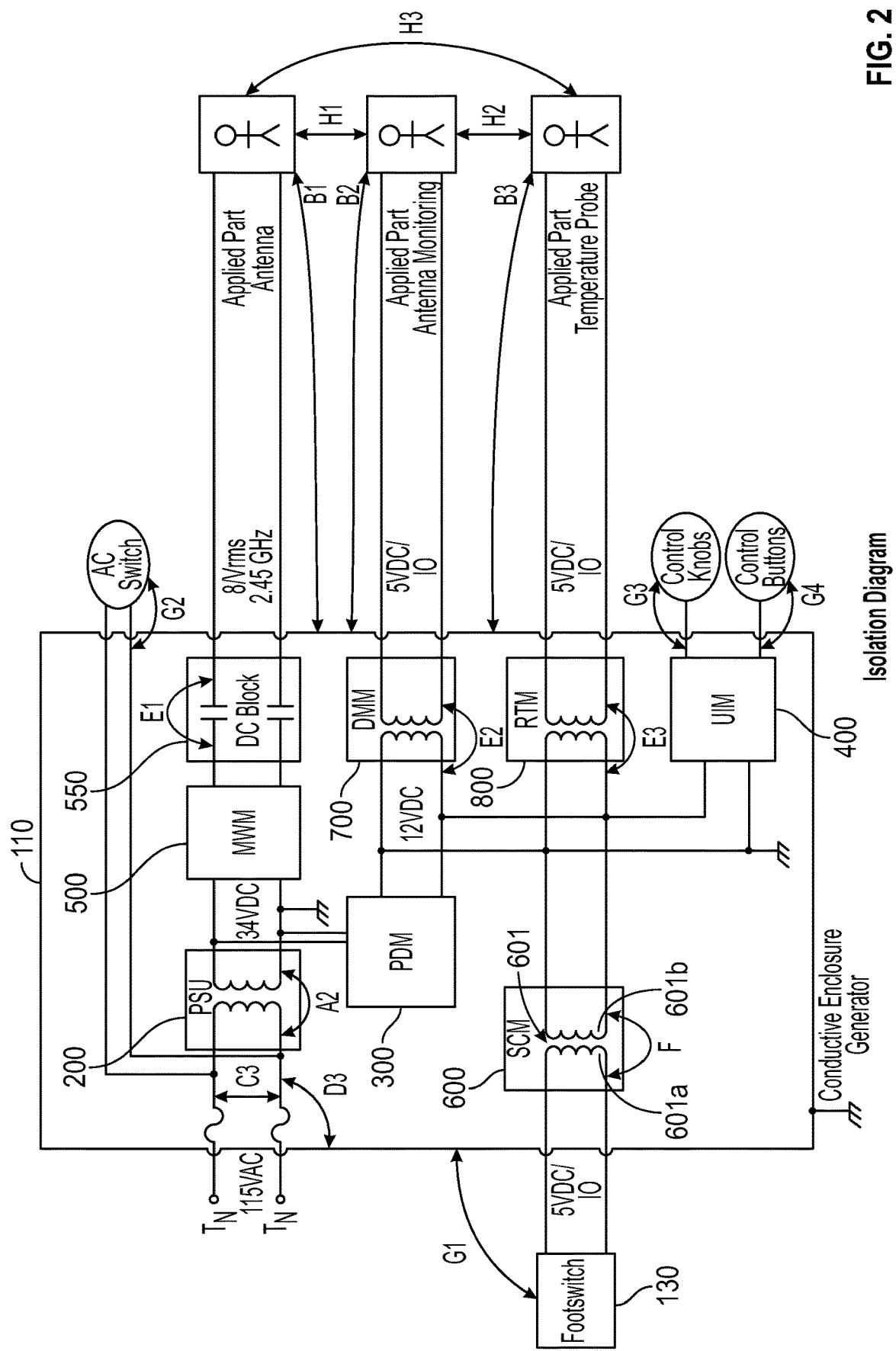
FIG. 2 is a circuit isolation diagram of the microwave ablation system of FIG. 1.
Figure 3:
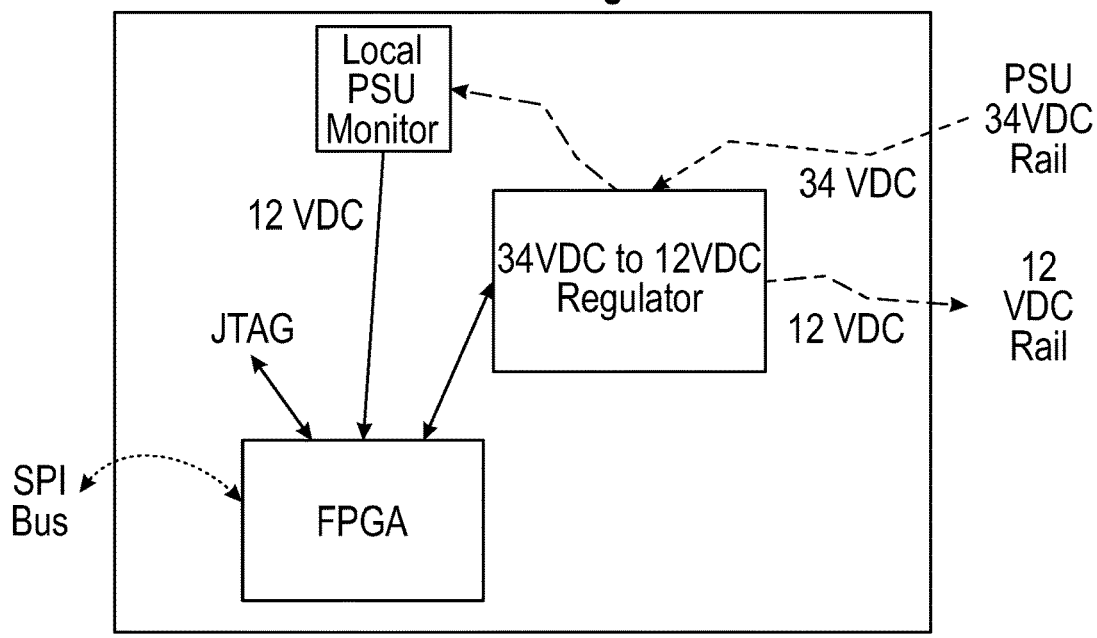
FIG. 3 is a block diagram of a power distribution module of the microwave generator of FIG. 1.
Figure 4:
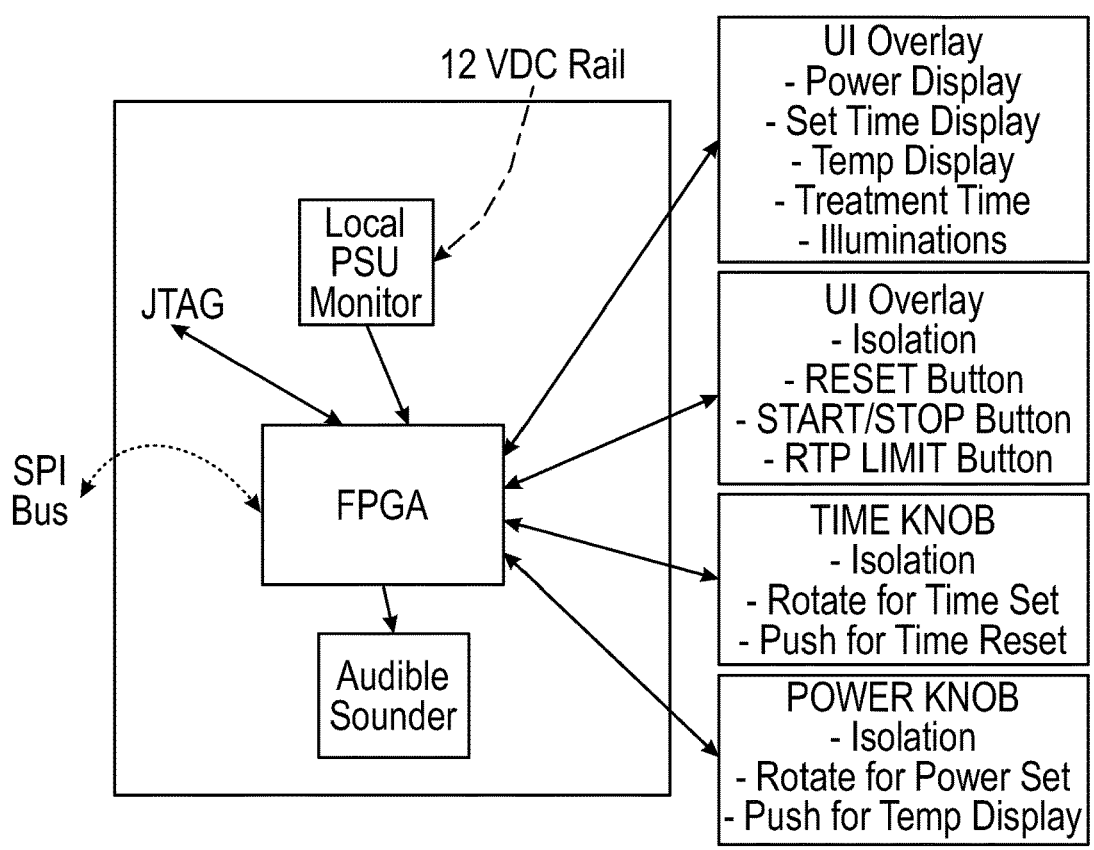
FIG. 4 is a block diagram of a user interface module of the microwave generator of FIG. 1.

FIG. 2 is a block diagram illustrating the isolation between each of the modules of the microwave generator 110 and the isolation between the modules of the microwave generator 110 and the patient. FIGS. 3-8 illustrate block diagrams of the power distribution module 300 (FIG. 3), the user interface module 400 (FIG. 4), the microwave module 500 (FIG. 5A), the system controller module 600 (FIG. 6), the device monitoring module 700 (FIG. 7), and the remote thermocouple module 800 (FIG. 8), respectively, of the microwave generator 110 (FIG. 1).

Figure 5A:
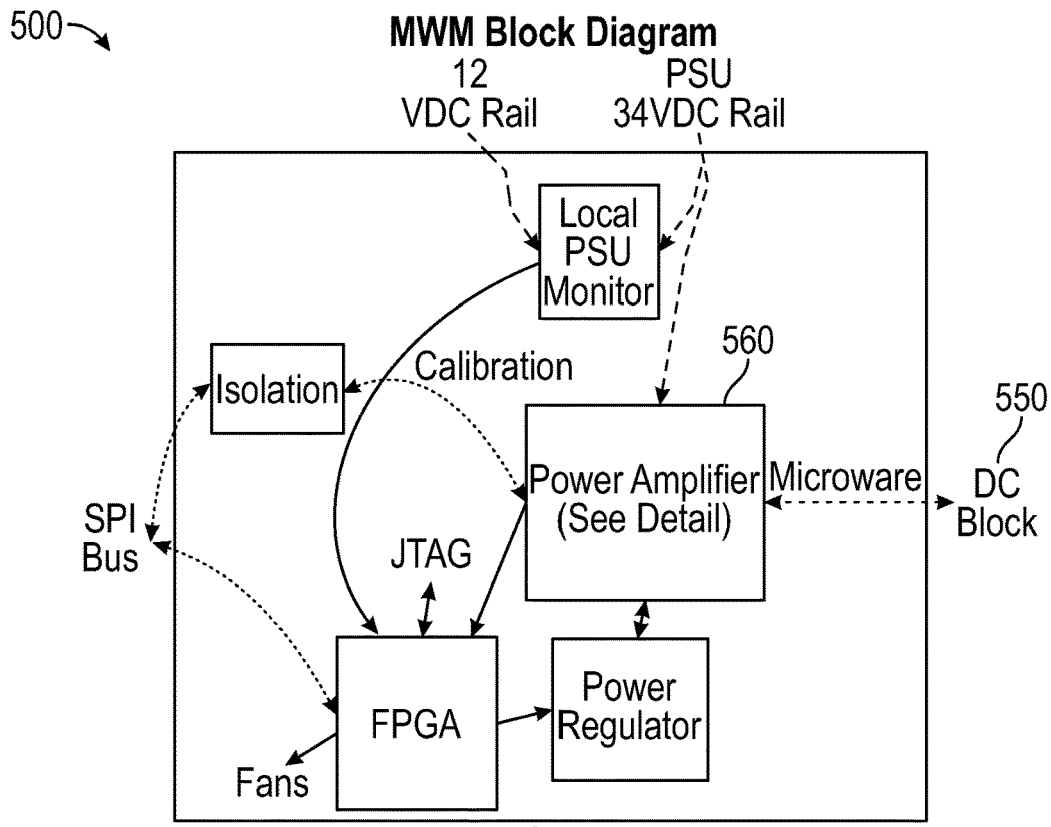
FIG. 5A is a block diagram of a microwave module of the microwave generator of FIG. 1.
Figure 5B:
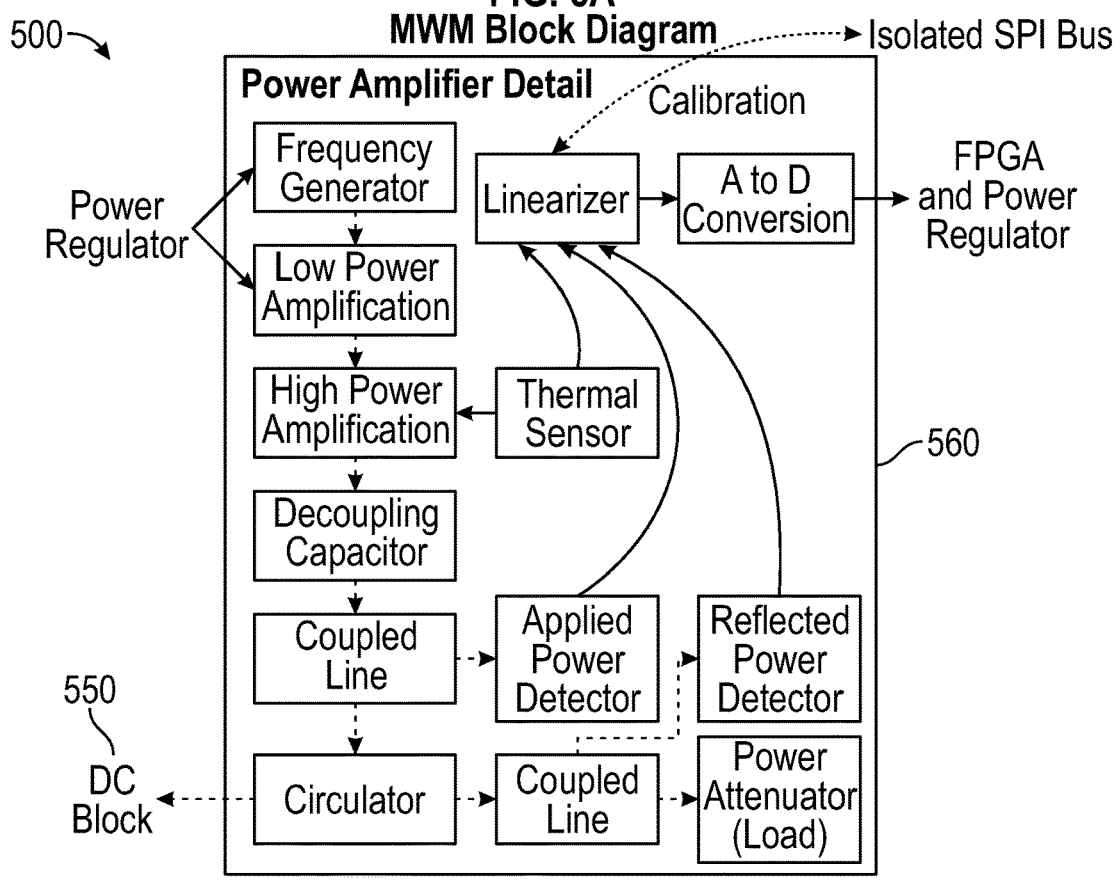
FIG. 5B is a block diagram of a power amplifier of the microwave module of FIG. 5A.
Figure 6:
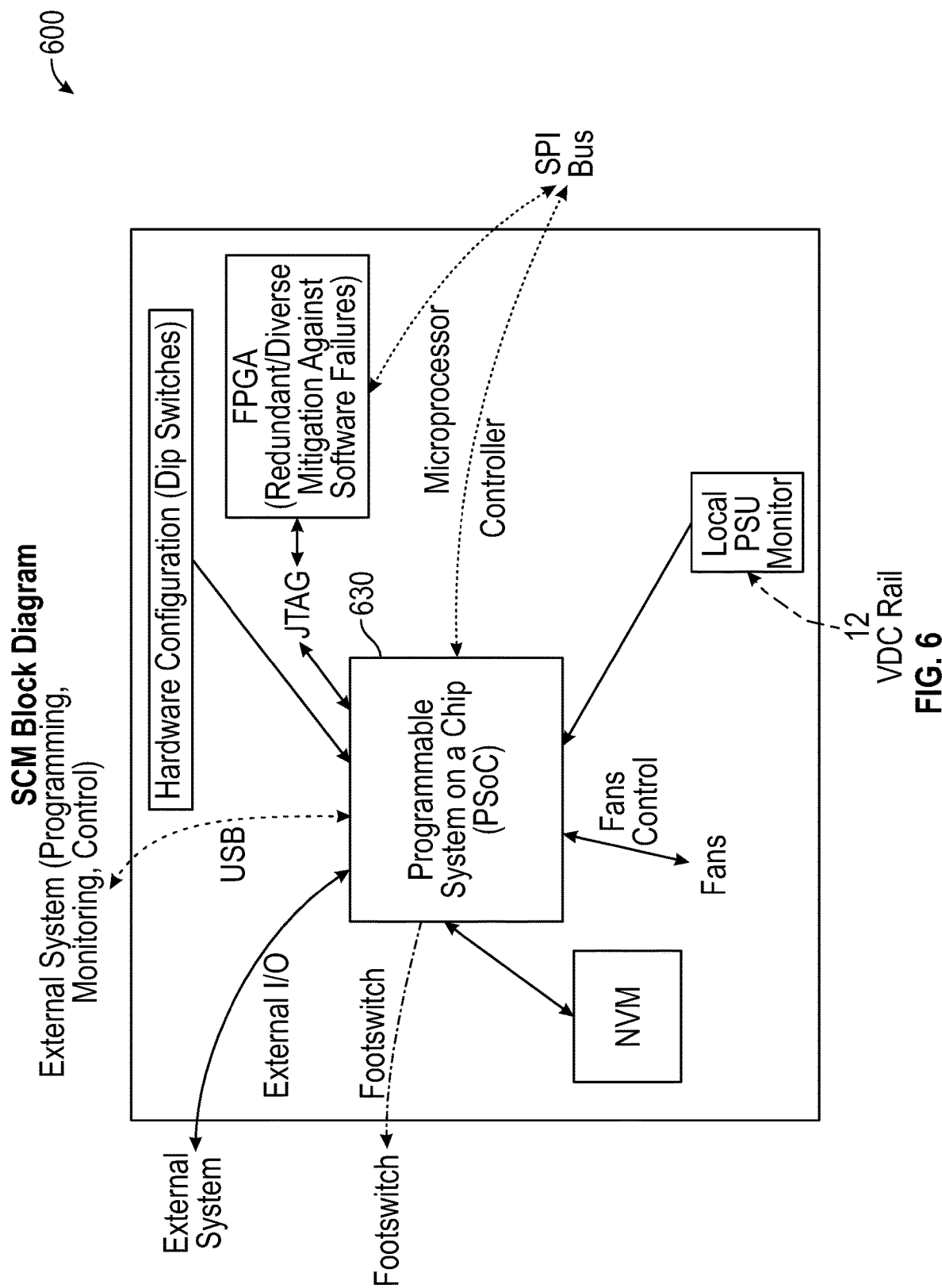
FIG. 6 is a block diagram of a system controller module of the microwave generator of FIG. 1.

FIG. 5A illustrates the microwave module 500 and patient isolator 550 of the microwave generator 110 according to an embodiment of the present disclosure. The microwave module 500 contains various components including a power amplifier 560 shown in detail in FIG. 5B. FIG. 6 illustrates the system controller module 600 of the microwave generator 110 according to an embodiment of the present disclosure. With brief reference to FIG. 2, the system controller module 600 includes an isolator 601. The isolator 601 may include a transformer having a primary winding 601a and a secondary winding 601b. Other isolation techniques are envisioned, such as optical. For the transformer isolation, power or signals received by the isolator 601 pass through the primary winding 601a of the transformer, which induces a current in the secondary winding 601b of the transformer proportional to the current received by the isolator 601. The induced current provides power or signals to/from the components of the system controller module 600, for example, the controller microprocessor 630. In an embodiment, the isolator 601 supplies power to an external system, for example, 5 VDC with a maximum power draw of 5 W. The isolator 601 may also isolate the operator utilizing accessories connected to the system controller module 600, such as the footswitch, from internal electronics of the microwave generator 110.

The controller microprocessor 630 is a programmable processor configured through flash programming, or through other suitable programming methods and languages, to communicate digitally with the microwave module 500, the device monitoring module 700, the remote thermocouple module 800, the user interface module 400, the footswitch 130, and other components of the microwave generator 110. The controller microprocessor 630 may be calibrated through software calibration methods including radix-based digital self-calibration, background equivalent radix extraction, interference cancelling, or hardware calibration methods including the use of, for example, comparator/digital-to-analog converter (DAC) combinations, digitally controllable low-pass filters using a digital potentiometer, calibration-multiplexers, or any hardware and/or software solutions, to improve the digital communications links. As part of its communication with the microwave module 500, the device monitoring module 700, the remote thermocouple module 800, and the user interface module 400, the controller microprocessor 630 communicates information regarding the controller microprocessor 630 including, for example, status information, serial number, and firmware version to each component, while receiving, from each component, information regarding the controller microprocessor 630 including, for example, status information, serial number, and firmware version, which the controller microprocessor 630 continually processes and monitors.

The controller microprocessor 630 digitally communicates with the user interface module 400 to receive user inputs and send information that may be communicated to a user by the user interface module 400. The controller microprocessor 630 may issue a signal to the user interface module 400 causing the user interface module 400 to prompt a user to enter a microwave power level or a treatment time. Upon user selection, the user interface module 400 sends the controller microprocessor 630 a signal indicating the selection and the controller microprocessor 630 receives and processes the signal before issuing a signal to the microwave module 500 to set the power level or treatment time. In the alternative, the controller microprocessor 630 may delay a signal to the microwave module 500. For instance, if the controller microprocessor 630 receives a treatment time, the controller microprocessor 630 sends a signal to the microwave module 500 only when the allotted time has ended. While the treatment occurs, the controller microprocessor 630 counts down the selected treatment time. In addition to issuing an end signal to the microwave module 500, the controller microprocessor 630 communicates with the user interface module 400 throughout the countdown to send the user interface module 400 information regarding the remaining treatment to display including the remaining treatment time to indicate to a user how much time remains.

Upon startup or at any time as requested by the system controller module 600 or by a user, the system controller module 600 may instruct the device monitoring module 700 to measure the DUID resistance of the energy applicator 120 and communicate the measured DUID resistance value to the system controller module 600. If the energy applicator 120 is identified as a smart device based on the measured DUID resistance of the energy applicator 120, the system controller module 600 may pass/request data packets to the device ID memory 126 of the energy applicator 120 via the reusable cable 115. Upon receipt of a requested data packet from, the device ID memory 126 of the energy applicator 120 responds by communicating the requested data packet.

Figure 7:
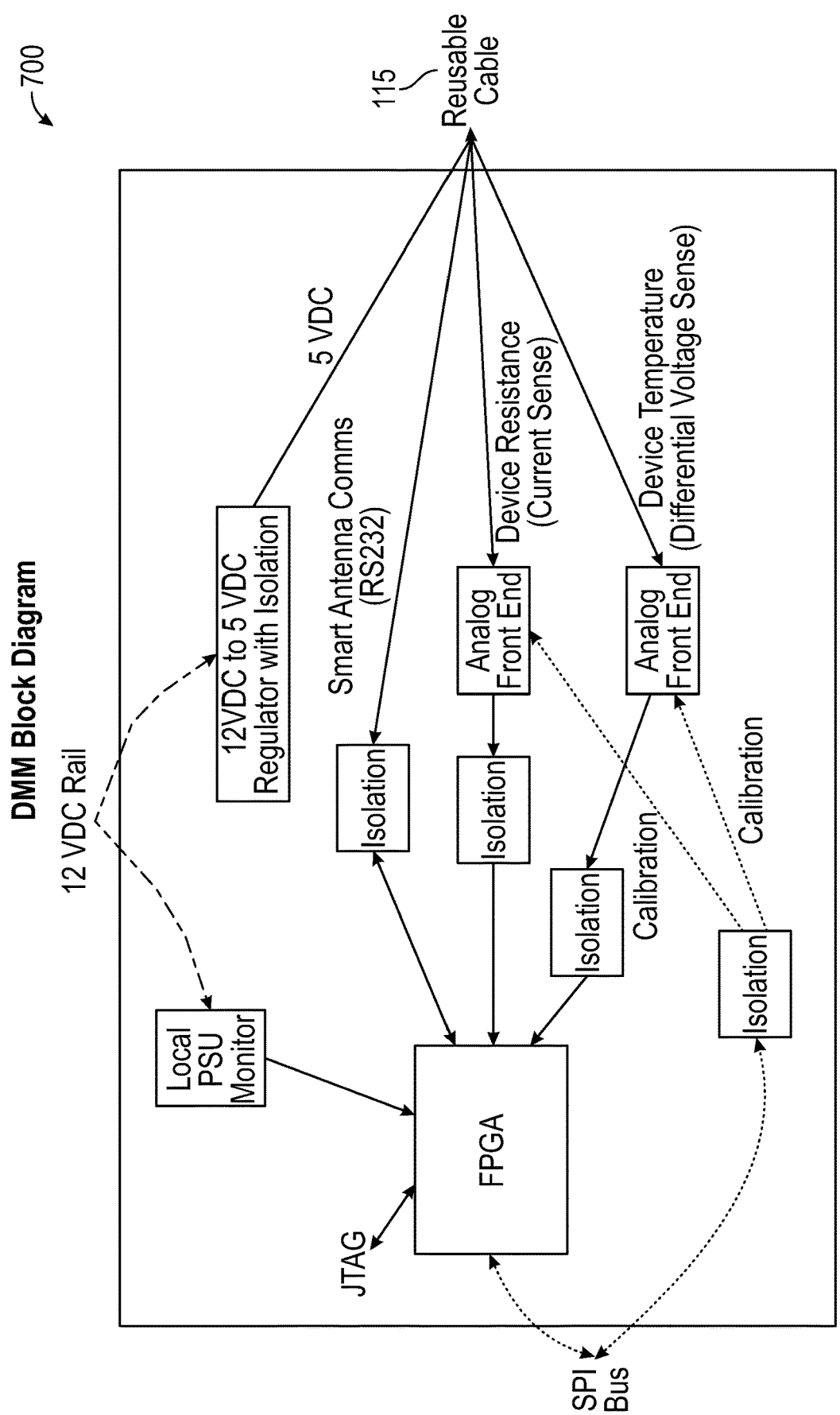
FIG. 7 is a block diagram of a device monitoring module of the microwave generator of FIG. 1.

FIG. 7 is a circuit block diagram of the device monitoring module 700 which couples to the energy applicator 120 (FIG. 1) via the reusable cable 115. Upon startup and with an energy applicator 120 connected to the microwave generator 110 via the reusable cable 115, the microwave generator 110 provides a precision current to the DUIR 124 (FIG. 1) via the reusable cable 115 to generate the DUID resistance value. The device monitoring module 700 measures the DUID resistance value and communicates this value to the system controller module 600 (FIG. 1). To identify the type of the energy applicator 120, the system controller module 600 processes the DUID resistance value received from the device monitoring module 700 and compares the processed DUID resistance value to a plurality of resistance value indicators stored in memory of the system controller module 600 that each correspond to a particular device type. The identified type of the energy applicator 120 may determine whether or not the connected device is compatible with the microwave generator 110. The type of a device may correspond to a particular capability of a device, a model of device, a particular series of a model of a device, a particular type of treatment modality of a device, whether or not a device is smart, a compatibility of a device with a microwave generator, or any combination of the foregoing. Device-specific operating thresholds for configuring operation of the microwave generator 110 for use with the energy applicator 120 may be determined based on the identified type of the energy applicator 120.

Figure 8:
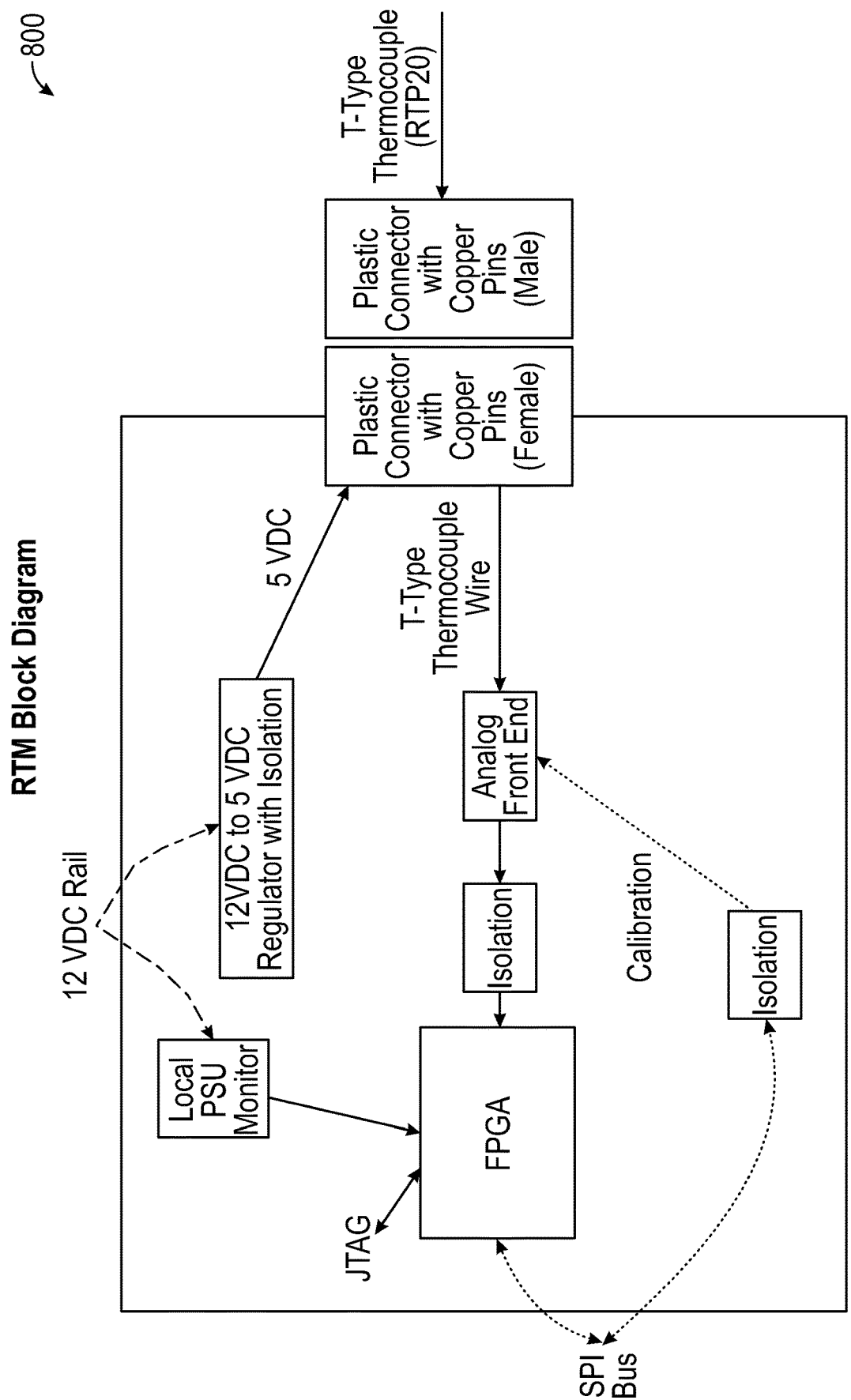
FIG. 8 is a block diagram of a remote thermocouple module of the microwave generator of FIG. 1.

FIG. 8 illustrates the remote thermocouple module 800 of the microwave generator 110 (FIG. 1). The remote thermocouple module 800 communicates with the remote thermocouple probe 140 (FIG. 1) to measure the temperature of the remote thermocouple probe 140. In particular, the remote thermocouple probe 140 includes a thermocouple junction which is created by welding the end of constantan (copper-nickel alloy) and copper wires together and placing the weld point at the desired measurement location. This junction of dissimilar metals creates a voltage proportional to the temperature of the junction. The copper and constantan wires are insulated behind the junction to maintain the voltage differential between the two wires. The remote thermocouple module 800 monitors this voltage differential to measure the temperature.

Figure 9:
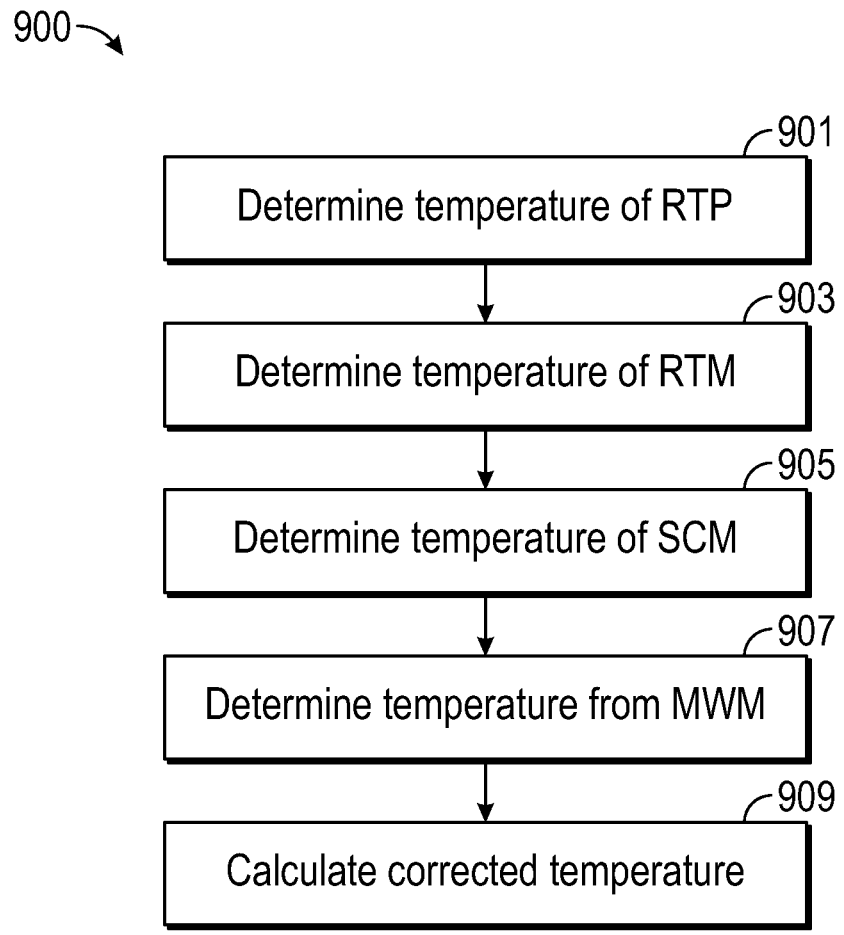
FIG. 9 is a flowchart illustrating a method of calculating a corrected temperature in accordance with the disclosure.

FIG. 9 illustrates a method for calculating a corrected temperature value and is described below as method 900. Although method 900 is described as including specific steps, method 900 may include some or all of the steps described. Additionally, although method 900 is described as being performed in an order of steps, the steps of method 900 may be performed in any order.

In an aspect, method 900 is performed by remote thermocouple module 800 (FIGS. 1 and 8), but method 900 may be performed, in part or in full, by any of the components or modules of microwave generator 110 (FIG. 1) or any component of microwave ablation system 100 (FIG. 1). For example, the remote thermocouple module 800 may include firmware that performs some or all of the steps of method 900.

Method 900 begins at step 901 where remote thermocouple module 800 determines a measured temperature value of a remote thermocouple probe 140 (RTP measured) which may be percutaneously inserted through a patient's skin adjacent a target site. In step 903, remote thermocouple module 800 determines a temperature value of itself (RTM), for example via a thermocouple attached to the remote thermocouple module 800. In step 905, remote thermocouple module 800 determines a temperature value of the system controller module 600 (SCM), for example, via a thermocouple attached to the system controller module 600. In step 907, remote thermocouple module 800 determines a temperature value of the microwave module 500, for example, via a thermocouple attached to the microwave module 500 (MWM). In an aspect, the temperature values described herein of each of the modules are directly delivered to the remote thermocouple module 800, although it is envisioned that remote thermocouple module 800 may retrieve the temperature values, or other values usable for calculating or determining the temperature values, from a bus that delivers data among the different module of the microwave generator 110.

In step 909, the corrected temperature value is calculated. The corrected temperature value (RTP corrected) is calculated based on the determined temperature value of the remote thermocouple probe 140 (RTP measured), the determined temperature value of the system controller module 600 (SCM), and at least one of the determined temperature value of the remote thermocouple module 800 (RTM) or the determined temperature value of the microwave module 500 (MWM).

In its simplest form, the corrected temperature value (RTP corrected) is calculated in step 909 using the formula:

$$RTP\ corrected = RTP\ measured - C1*(RTM-SCM),$$
$$where\ C1=0.3.$$

Further improvement in accuracy can be achieved by considering the state of the microwave generator 110 (e.g., active, idle, etc.) and factoring four temperature variables. Thus, in an aspect, method 900 includes a step of determining whether the microwave generator 110 is in an idle state or an active state. When it is determined that the microwave generator 110 is in the idle state, the corrected temperature value (RTP corrected) is calculated using the formula:

$$RTP\ corrected = RTP\ measured - C1*(RTM-SCM),$$
$$where\ C1=0.3.$$

Additionally, when it is determined that the microwave generator 110 is in the active state, the corrected temperature value (RTP corrected) is calculated using the formula:

$$RTP\ corrected = RTP\ measured - C2*(MWM-SCM),$$
$$where\ C1=0.13.$$

Even further improvement in the accuracy is achieved when factoring the duration of activation and the duration from deactivation of the microwave generator 110. For example, more time-based correction algorithms with four temperature variables are envisioned which handle the transitional states when the microwave generator 110 is rapidly heating or cooling down. When it is determined that the microwave generator 110 is in the idle state and not within 120 seconds of deactivation, the corrected temperature value (RTP corrected) is calculated using the formula:

$$RTP\ corrected = RTP\ measured - C1*(RTM-SCM),$$
$$where\ C=0.3.$$

Additionally, when it is determined that the microwave generator 110 is in the idle state and within 120 seconds of deactivation, the corrected temperature value (RTP corrected) is calculated using the formula:

$$RTP\ corrected = RTP\ measured - C6*(RTM-SCM),$$
$$where\ C6=0.19.$$

When it is determined that the microwave generator 110 is in the active state and within 10 seconds of activation, the corrected temperature value (RTP corrected) is calculated using the formula:

$$RTP\ corrected = RTP\ measured - C1*(RTM-SCM) - C2*(MWM-SCM),\ where\ C1=0.3\ and\ C2=0.26.$$

When it is determined that the microwave generator 110 is in the active state and between 10 to 30 seconds of activation, the corrected temperature value (RTP corrected) is calculated using the formula:

$$RTP\ corrected = RTP\ measured - C1*(RTM-SCM) - C3*(MWM-SCM),\ where\ C=0.3\ and\ C3=0.21.$$

When it is determined that the microwave generator 110 is in the active state and between 30 to 120 seconds of activation, the corrected temperature value (RTP corrected) is calculated using the formula:

$$RTP\ corrected = RTP\ measured - C1*(RTM-SCM) - C4*(MWM-SCM),\ where\ C=0.3\ and\ C4=0.15.$$

When it is determined that the microwave generator 110 is in the active state and after 120 seconds of activation, the corrected temperature value (RTP corrected) is calculated using the formula:

$$RTP\ corrected = RTP\ measured - C1*(RTM-SCM) - C5*(MWM-SCM),\ where\ C1=0.3\ and\ C5=0.09.$$

Even further accuracy may be achieved by factoring four temperature variables as well as the output power level and elapsed activation time to scale the correction factors. Thus, in an aspect, the method includes determining an elapsed activation time (T) and an output power level (P) of the microwave generator 110, and the corrected temperature value (RTP corrected) is calculated using the formula:

$$RTP\ corrected = RTP\ measured - C1*(RTM-SCM) - P*1/T*C2*(MWM-SCM),\ where\ C1=0.3\ and\ C2=0.02.$$

Figure 10:
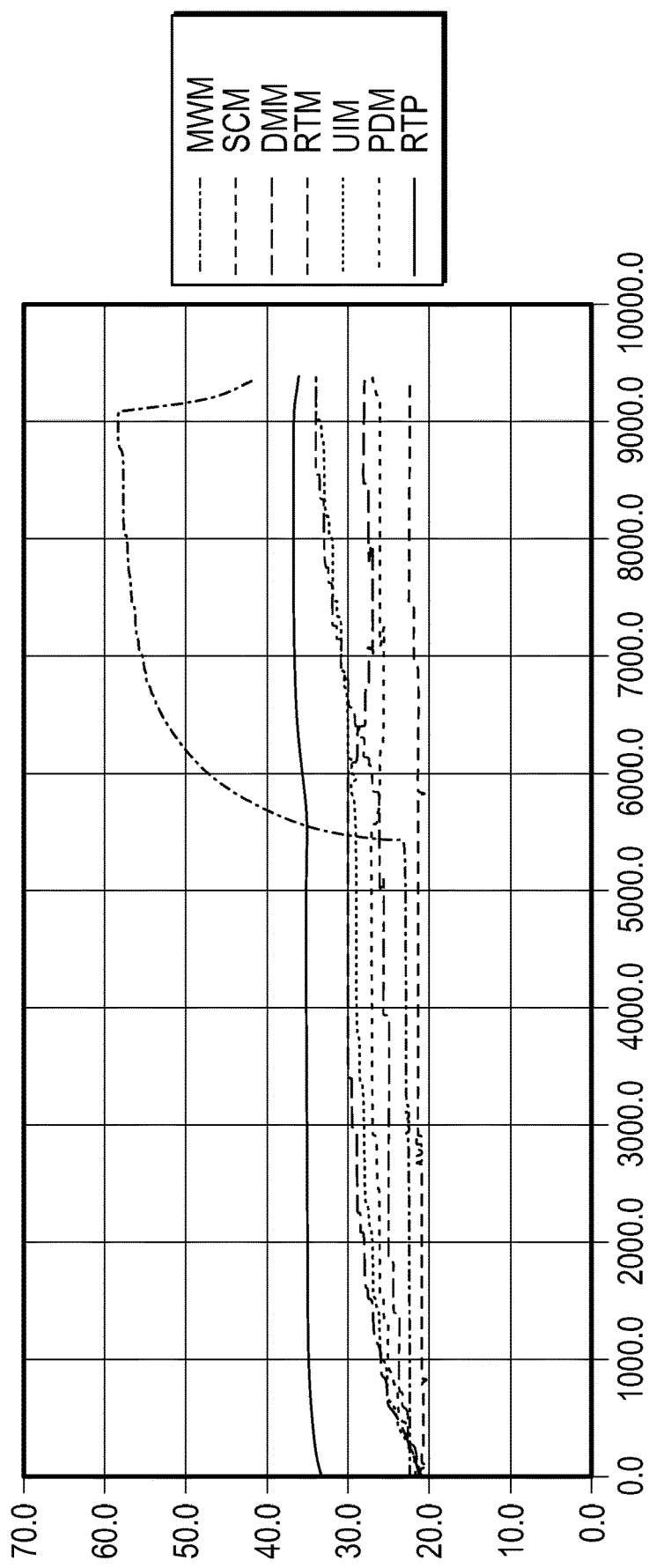
FIG. 10 is a graph illustrating experimental results of errors in calculating temperature measurements caused by parasitic conditions.

FIG. 10 is a chart illustrating various temperature measurements of the modules of the microwave generator 110 (FIG. 1) during operation, which demonstrates the inaccurate temperature readings, for example, caused by parasitic junctions and other factors during operation of the microwave generator 110. Temperatures of each module (PDM, SCM, DMM, UIM MWM, RTM) along with the RTP temperature measurements are shown. The time begins with startup of the microwave generator 110, allows the microwave generator 110 to reach steady state, and then a roughly 10-minute-long high output power (150W) microwave energy activation is completed (easily denoted by rise in MWM temperature). As can be seen in FIG. 10, the RTP temperature which should remain constant in this test is affected by both the microwave generator 110 starting out cold, then reaching steady state temperature on startup and then by the heating from the microwave amplifier during an energy activation. The SCM remains closest to ambient temperature, due to its proximity to enclosure cooling fans which bring air into the microwave generator 110 from outside. The MWM has the largest increase in temperature due to its generation of microwave power. This suggests the MWM and SCM can provide insightful inputs to the correction algorithm. The RTM temperature is also insightful, as it is in closest proximity to a parasitic thermocouple junction on a bulkhead plastic connector within the microwave generator 110 front panel. The correction algorithms described above enable the correction of the inaccuracies caused by operation of the microwave generator 110 over time and the parasitic junctions present in the microwave generator 110.

The microwave generator 110 is designed to operate in 10-30 dC room temperatures and the thermal environment within a microwave generator 110 is dynamic due to the heating from the AC/DC and DC/DC and DC/MW power supplies. As the microwave generator 110 is powered on and idle, the AC/DC and DC/DC power supplies begin to slowly heat the enclosure, and when microwaves are generated, a dramatic temperature rise can occur within the enclosure from the DC/MW supply (roughly half of the power consumed by a microwave amplifier is dissipated as heat in the amplifier itself). Various fans are used to cool the microwave generator 110 which may be dynamically controlled based on temperature (e.g., the fan speed may be lower when the microwave generator 110 is cooler to minimize the fan sound and raised to deliver more cooling performance as module temperatures within the generator rise).

The formulas and methods described above are not limiting in the scope of the disclosure. Algorithms using exponential or logarithmic functions and use of more than four temperature variables from the microwave generator 110, as well as consideration of cooling fan speed are also envisioned. Additionally, to get a better ambient temperature reading, an embodiment is envisioned whereby the user is instructed to place the tip of the remote thermocouple probe 140 on a metal plate or similar feature on the microwave generator 110 front panel. This measurement could further improve the correction algorithm with a higher confidence ambient temperature reading (instead of using the SCM temperature).

While several embodiments of the disclosure have been shown in the drawings and/or discussed herein, it is not intended that the disclosure be limited thereto, as it is intended that the disclosure be as broad in scope as the art will allow and that the specification be read likewise.

Therefore, the above description should not be construed as limiting, but merely as exemplifications of particular embodiments. Those skilled in the art will envision other modifications within the scope and spirit of the claims appended hereto.

What is claimed is:

1. A method for calculating a corrected temperature value by a microwave generator, the method comprising:
   determining a measured temperature value from a remote thermocouple probe (RTP measured);
   determining a temperature value of a remote thermocouple module (RTM);
   determining a temperature value of a system controller module (SCM);
   determining a temperature value of a microwave module (MWM); and
   calculating the corrected temperature value (RTP corrected) based on the determined temperature value of the remote thermocouple probe (RTP measured), the determined temperature value of the system controller module (SCM), and at least one of the determined temperature value of the remote thermocouple module (RTM) or the determined temperature value of the microwave module (MWM).

2. The method according to claim 1, wherein the corrected temperature value (RTP corrected) is calculated using the formula:

RTP corrected=RTP measured−$C1$*(RTM−SCM), where $C1=0.3$.

3. The method according to claim 1, further comprising determining whether the microwave generator is in an idle state or an active state.

4. The method according to claim 3, wherein:
   when it is determined that the microwave generator is in the idle state, the corrected temperature value (RTP corrected) is calculated using the formula:

RTP corrected=RTP measured−$C1$*(RTM−SCM), where $C1=0.3$; and when it is determined that the microwave generator is in the active state, the corrected temperature value (RTP corrected) is calculated using the formula:

RTP corrected=RTP measured−$C2$*(MWM−SCM), where $C1=0.13$.

5. The method according to claim 3, wherein:
   when it is determined that the microwave generator is in the idle state and not within 120 seconds of deactivation, the corrected temperature value (RTP corrected) is calculated using the formula:

RTP corrected=RTP measured−$C1$*(RTM−SCM), where $C1=0.3$; and when it is determined that the microwave generator is in the idle state and within 120 seconds of deactivation, the corrected temperature value (RTP corrected) is calculated using the formula:

RTP corrected=RTP measured−$C6$*(RTM−SCM), where $C6=0.19$.

6. The method according to claim 3, wherein:
   when it is determined that the microwave generator is in the active state and within 10 seconds of activation, the corrected temperature value (RTP corrected) is calculated using the formula:

RTP corrected=RTP measured−$C1$*(RTM−SCM)−$C2$*(MWM−SCM), where $C1=0.3$ and $C2=0.26$.

7. The method according to claim 3, wherein:
   when it is determined that the microwave generator is in the active state and between 10 to 30 seconds of activation, the corrected temperature value (RTP corrected) is calculated using the formula:

RTP corrected=RTP measured−$C1$*(RTM−SCM)−$C3$*(MWM−SCM), where $C=0.3$ and $C3=0.21$.

8. The method according to claim 3, wherein:
   when it is determined that the microwave generator is in the active state and between 30 to 120 seconds of activation, the corrected temperature value (RTP corrected) is calculated using the formula:

RTP corrected=RTP measured−$C1$*(RTM−SCM)−$C4$*(MWM−SCM), where $C1=0.3$ and $C4=0.15$.

9. The method according to claim 3, wherein:
   when it is determined that the microwave generator is in the active state and after 120 seconds of activation, the corrected temperature value (RTP corrected) is calculated using the formula:

RTP corrected=RTP measured−$C1$*(RTM−SCM)−$C5$*(MWM−SCM), where $C1=0.3$ and $C5=0.09$.

10. The method according to claim 1, further comprising determining an elapsed activation time (T) and an output power level of the microwave generator (P), wherein the corrected temperature value (RTP corrected) is calculated using the formula:

RTP corrected=RTP measured−$C1$*(RTM−SCM)−$P*1/T*C2$*(MWM−SCM), where $C1=0.3$ and $C2=0.02$.

11. A microwave generator comprising:
    a system controller module configured to control the microwave generator;
    a microwave module configured to generate microwave energy;
    a remote thermocouple module configured to determine a temperature value of a remote thermocouple probe (RTP measured);

wherein at least one of the system controller module or the remote thermocouple module is configured to:
- determine a temperature value of the remote thermocouple module (RTM);
- determine a temperature value of the system controller module (SCM);
- determine a temperature value of the microwave module (MWM); and
- calculate a corrected temperature value (RTP corrected) based on the determined temperature value of the remote thermocouple probe (RTP measured), the determined temperature value of the system controller module (SCM), and at least one of the determined temperature value of the remote thermocouple module (RTM) or the determined temperature value of the microwave module (MWM).

12. The microwave generator according to claim 11, wherein the corrected temperature value (RTP corrected) is calculated using the formula:

$$RTP\ corrected=RTP\ measured-C1*(RTM-SCM),$$
where $C1=0.3$.

13. The microwave generator according to claim 11, wherein at least one of the system controller module or the remote thermocouple module is configured to determine whether the microwave generator is in an idle state or an active state.

14. The microwave generator according to claim 13, wherein:
- when it is determined that the microwave generator is in the idle state, the corrected temperature value (RTP corrected) is calculated using the formula:

$$RTP\ corrected=RTP\ measured-C1*(RTM-SCM),$$
where $C1=0.3$; and

- when it is determined that the microwave generator is in the active state, the corrected temperature value (RTP corrected) is calculated using the formula:

$$RTP\ corrected=RTP\ measured-C2*(MWM-SCM),$$
where $C1=0.13$.

15. The microwave generator according to claim 13, wherein:
- when it is determined that the microwave generator is in the idle state and not within 120 seconds of deactivation, the corrected temperature value (RTP corrected) is calculated using the formula:

$$RTP\ corrected=RTP\ measured-C1*(RTM-SCM),$$
where $C1=0.3$; and

- when it is determined that the microwave generator is in the idle state and within 120 seconds of deactivation, the corrected temperature value (RTP corrected) is calculated using the formula:

$$RTP\ corrected=RTP\ measured-C6*(RTM-SCM),$$
where $C6=0.19$.

16. The microwave generator according to claim 13, wherein:
- when it is determined that the microwave generator is in the active state and within 10 seconds of activation, the corrected temperature value (RTP corrected) is calculated using the formula:

$$RTP\ corrected=RTP\ measured-C1*(RTM-SCM)-C2*(MWM-SCM),\ where\ C1=0.3\ and\ C2=0.26.$$

17. The microwave generator according to claim 13, wherein:
- when it is determined that the microwave generator is in the active state and between 10 to 30 seconds of activation, the corrected temperature value (RTP corrected) is calculated using the formula:

$$RTP\ corrected=RTP\ measured-C1*(RTM-SCM)-C3*(MWM-SCM),\ where\ C1=0.3\ and\ C3=0.21.$$

18. The microwave generator according to claim 13, wherein:
- when it is determined that the microwave generator is in the active state and between 30 to 120 seconds of activation, the corrected temperature value (RTP corrected) is calculated using the formula:

$$RTP\ corrected=RTP\ measured-C1*(RTM-SCM)-C4*(MWM-SCM),\ where\ C1=0.3\ and\ C4=0.15;\ and$$

- when it is determined that the microwave generator is in the active state and after 120 seconds of activation, the corrected temperature value (RTP corrected) is calculated using the formula:

$$RTP\ corrected=RTP\ measured-C1*(RTM-SCM)-C5*(MWM-SCM),\ where\ C1=0.3\ and\ C5=0.09.$$

19. The microwave generator according to claim 11, wherein at least one of the system controller module or the remote thermocouple module is further configured to determine an elapsed activation time (T) and an output power level of the microwave generator (P), wherein the corrected temperature value (RTP corrected) is calculated using the formula:

$$RTP\ corrected=RTP\ measured-C1*(RTM-SCM)-P*1/T*C2*(MWM-SCM),\ where\ C1=0.3\ and\ C2=0.02.$$

20. A non-transitory computer-readable storage medium storing instructions, which when executed by a processor, cause the processor to perform a method for calculating a corrected temperature value, the method comprising:
- determining a measured temperature value from a remote thermocouple probe (RTP measured);
- determining a temperature value of a remote thermocouple module (RTM);
- determining a temperature value of a system controller module (SCM);
- determining a temperature value of a microwave module (MWM); and
- calculating the corrected temperature value (RTP corrected) based on the determined temperature value of the remote thermocouple probe (RTP measured), the determined temperature value of the system controller module (SCM), and at least one of the determined temperature value of the remote thermocouple module (RTM) or the determined temperature value of the microwave module (MWM).

* * * * *